US011691134B2

(12) United States Patent
Berthout et al.

(10) Patent No.: US 11,691,134 B2
(45) Date of Patent: Jul. 4, 2023

(54) CATALYST COMPRISING A MIXTURE OF AN AFX-STRUCTURE ZEOLITE AND A BEA-STRUCTURE ZEOLITE AND AT LEAST ONE TRANSITION METAL FOR SELECTIVE REDUCTION OF NOX

(71) Applicant: IFP Energies nouvelles, Rueil-Malmaison (FR)

(72) Inventors: David Berthout, Rueil-Malmaison (FR); Bogdan Harbuzaru, Rueil-Malmaison (FR); Eric Llido, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 88 days.

(21) Appl. No.: 17/058,026

(22) PCT Filed: May 16, 2019

(86) PCT No.: PCT/EP2019/062563
§ 371 (c)(1),
(2) Date: Nov. 23, 2020

(87) PCT Pub. No.: WO2019/224090
PCT Pub. Date: Nov. 28, 2019

(65) Prior Publication Data
US 2021/0205797 A1  Jul. 8, 2021

(30) Foreign Application Priority Data
May 24, 2018 (FR) ........................................ 1854382

(51) Int. Cl.
| | | |
|---|---|---|
| *B01J 29/80* | (2006.01) |
| *B01D 53/94* | (2006.01) |
| *B01J 29/76* | (2006.01) |
| *B01J 35/04* | (2006.01) |
| *B01J 37/00* | (2006.01) |
| *B01J 37/02* | (2006.01) |
| *B01J 37/03* | (2006.01) |
| *B01J 37/04* | (2006.01) |
| *B01J 37/08* | (2006.01) |
| *B01J 37/10* | (2006.01) |
| *C07D 295/037* | (2006.01) |
| *F01N 3/20* | (2006.01) |
| *F01N 3/28* | (2006.01) |

(52) U.S. Cl.
CPC .......... *B01J 29/80* (2013.01); *B01D 53/9418* (2013.01); *B01J 29/7615* (2013.01); *B01J 35/04* (2013.01); *B01J 37/0045* (2013.01); *B01J 37/0246* (2013.01); *B01J 37/038* (2013.01); *B01J 37/04* (2013.01); *B01J 37/082* (2013.01); *B01J 37/10* (2013.01); *C07D 295/037* (2013.01); *F01N 3/2066* (2013.01); *F01N 3/2803* (2013.01); *B01D 2255/20738* (2013.01); *B01D 2255/20761* (2013.01); *B01D 2255/502* (2013.01); *B01D 2255/9155* (2013.01); *B01J 2229/186* (2013.01); *F01N 2330/02* (2013.01); *F01N 2370/04* (2013.01)

(58) Field of Classification Search
None
See application file for complete search history.

(56) References Cited

U.S. PATENT DOCUMENTS

| | | | |
|---|---|---|---|
| 9,687,829 B2 * | 6/2017 | McGuire | B01J 29/80 |
| 2012/0275977 A1 * | 11/2012 | Chandler | B01J 29/0354 |
| | | | 60/299 |
| 2015/0328625 A1 * | 11/2015 | Van Donk | B01J 35/1038 |
| | | | 502/64 |
| 2015/0367337 A1 * | 12/2015 | Yang | B01J 29/763 |
| | | | 423/239.2 |
| 2016/0096169 A1 | 4/2016 | Rivas-Cardona et al. | |
| 2016/0137518 A1 | 5/2016 | Rivas-Cardona et al. | |
| 2017/0274366 A1 * | 9/2017 | Teranishi | F01N 3/0222 |
| 2018/0093259 A1 | 4/2018 | Chen et al. | |
| 2018/0111086 A1 * | 4/2018 | Chen | B01D 53/9436 |

FOREIGN PATENT DOCUMENTS

| | | | |
|---|---|---|---|
| CN | 102671691 | * | 9/2012 |
| JP | 2014-148441 A | | 8/2014 |
| WO | 2016/205509 A1 | | 12/2016 |
| WO | 2017/080722 A1 | | 5/2017 |
| WO | 2017/087385 A1 | | 5/2017 |
| WO | 2017/202495 A1 | | 11/2017 |

OTHER PUBLICATIONS

International Search Report for PCT/EP2019/062563, dated Sep. 9, 2019; English translation submitted herewith (6 pgs.).
Martin Nuria et al. "Cage-based small-pore catalysts for NH3-SCR prepared by combining bulky organic structure directing agents with modified zeolites as reagents" Applied Catalysis B: Environmental, Elsevier, Amsterdam, NL, vol. 217, May 29, 2017 (May 29, 2017), pp. 125-136 DOI: 10.1016/J.APCATB.2017.05.082 ISSN: 0926-3373, XP085112832.
Dustin W Fickel et al. "The ammonia selective catalytic reduction activity of copper-exchanged small-pore zeolites" Applied Catalysis B: Environmental, Elsevier, Amsterdam, NL, vol. 102, No. 3, Dec. 9, 2010 (Dec. 9, 2010), pp. 441-448, [retrieved on Dec. 16, 2010] DOI: 10.1016/J.APCATB.2010.12.022 ISSN: 0926-3373, XP028139896.

(Continued)

*Primary Examiner* — Sheng H Davis
(74) *Attorney, Agent, or Firm* — Fitch, Even, Tabin & Flannery LLP

(57) ABSTRACT

The invention relates to a catalyst comprising a mixture of AFX-structure and BEA-structure zeolites and at least one additional transition metal, to the process for preparing same and to the use thereof for the selective catalytic reduction of NOx in the presence of a reducing agent such as $NH_3$ or $H_2$.

27 Claims, 1 Drawing Sheet

(56) References Cited

OTHER PUBLICATIONS

Wang Aiyong et al. NH3- SCR on Cu, Fe and Cu+Fe exchanged beta and SSZ-13 catalysts: Hydrothermal aging and propylene poisoning effects Catalysis Today, vol. 320, Oct. 7, 2017 (Oct. 7, 2017), pp. 91-99 DOI: 10.1016/J.CATTOD.2017.09.061 ISSN: 0920-5861, XP085513181.

* cited by examiner

CATALYST COMPRISING A MIXTURE OF AN AFX-STRUCTURE ZEOLITE AND A BEA-STRUCTURE ZEOLITE AND AT LEAST ONE TRANSITION METAL FOR SELECTIVE REDUCTION OF NOX

CROSS-REFERENCE TO RELATED APPLICATIONS

This application is a U.S. national phase application filed under 35 U.S.C. § 371 of International Application No. PCT/EP2019/062563, filed May 16, 2019, designating the United States, which claims priority from French Patent Application No. 18/54.382, filed May 24, 2018, which are hereby incorporated herein by reference in their entirety.

TECHNICAL FIELD OF THE INVENTION

The subject of the invention is a process for preparing a catalyst based on an intimate mixture of an AFX-structure zeolite and a BEA-structure zeolite, and at least one transition metal, the catalyst prepared or capable of being prepared by the process, and the use thereof for the selective catalytic reduction of NOx in the presence of a reducing agent, in particular in internal combustion engines.

PRIOR ART

Emissions of nitrogen oxides (NOx) resulting from the combustion of fossil fuels are a serious concern for society. Increasingly stringent standards have been put in place by government authorities in order to limit the impact of combustion emissions on the environment and on health. For light vehicles in Europe, under the Euro 6c standard, emissions of NOx and of particles must not exceed a very low level in all operating conditions. The new WLTC test cycle (Worldwide Harmonized Light Vehicles Test Cycle) and the regulation of Real Driving Emissions (RDE) combined with compliance factors require the development of a highly effective emission control system in order to meet these targets. Selective catalytic reduction (SCR) has emerged as an effective technology for removing nitrogen oxides from oxygen-rich exhaust gases that are typical of diesel and positive-ignition engines in lean-mixture mode. Selective catalytic reduction is carried out with a reducing agent, generally ammonia, and can therefore be referred to as $NH_3$—SCR. The ammonia ($NH_3$) involved in the SCR process is usually generated via the decomposition of an aqueous urea solution (AdBlue or DEF) and produces $N_2$ and $H_2O$ when reacted with NOx.

Zeolites exchanged with transition metals are used in particular as catalysts for $NH_3$—SCR applications in transport. Small-pore zeolites, particularly copper-exchanged chabazites, are particularly suitable. They exist commercially in the form of silico-aluminophosphate Cu-SAPO-34 and aluminosilicates Cu—SSZ-13 (or Cu—SSZ-62). Their hydrothermal resistance and NOx conversion efficiency makes them the current standards. However, as the standards become increasingly restrictive, there is a need to further improve the performance of the catalysts.

The use of AFX-structure zeolites for $NH_3$—SCR applications is known, but few studies evaluate the efficiency of catalysts that use this zeolite.

Fickel et al. (Fickel, D. W., & Lobo, R. F. (2009), The Journal of Physical Chemistry C, 114(3), 1633-1640) studies the use of a copper-exchanged SSZ-16 (with AFX structure) for NOx removal. This zeolite is synthesized in accordance with U.S. Pat. No. 5,194,235, in which copper is introduced by exchange using copper(II) sulfate at 80° C. for 1 h. Recent results (Fickel, D. W., D'Addio, E., Lauterbach, J. A., & Lobo, R. F. (2011), 102(3), 441-448) show excellent conversion and good hydrothermal resistance for copper loading at 3.78% by weight.

Work on the synthesis of AFX-structure zeolites has been carried out with various structural agents (Lobo, R. F., Zones, S. I., & Medrud, R. C. (1996), Chemistry of Materials, 8(10), 2409-2411) as well as synthesis optimization work (Hrabanek, P., Zikanova, A., Supinkova, T., Drahokoupil, J., Fila, V., Lhotka, M., Bernauer, B. (2016), Microporous and Mesoporous Materials, 228, 107-115).

Wang et al. (Wang, D. et al., CrystEngComm., (2016), 18(6), 1000-1008) have studied the replacement of the TMHD structuring agent with a TEA-TMA mixture for the formation of SAPO-56 and obtained unwanted SAPO-34 and SAPO-20 phases. The incorporation of transition metals is not discussed.

Patent US 2016/0137518 describes a quasi-pure AFX zeolite, its synthesis from sources of silica and alumina in the presence of a 1,3-bis(1-adamantyl)imidazolium hydroxide structuring agent, the preparation of a catalyst based on the AFX zeolite exchanged with a transition metal, and its use for $NH_3$—SCR applications. No particular form of AFX zeolite is mentioned.

More recently, patent US 2018/0093259 describes the synthesis of small-pore zeolites, such as the AFX-structure zeolite, from FAU-type zeolite in the presence of a structuring agent, such as 1,3-bis(1-adamantyl)imidazolium hydroxide, and a source of alkaline-earth metal. It also describes applications of the AFX-structure zeolite obtained, in particular the use of this zeolite as an NOx reduction catalyst, following exchange with a metal such as iron. In parallel, patent US 2016/0096169A1 describes the use in NOx conversion of a catalyst based on an AFX-structure zeolite having an Si/Al ratio of 15 to 50 exchanged with a metal, the AFX zeolite being obtained starting from a structuring agent of 1,3-bis(1-adamantyl)imidazolium hydroxide type. The results obtained, in NOx conversion, show in particular a selectivity of the catalysts prepared in accordance with patents US 2018/0093259 and US 2016/0096169 to nitrous oxide not exceeding 20 ppm.

Document JP 2014-148441 describes the synthesis of a solid related to an AFX zeolite, in particular a copper-containing SAPO-56 which can be used for $NO_x$ reduction. The solid is synthesized and then added to a mixture comprising an alcohol and a copper salt, the whole mixture being calcined. The copper is thus added after the formation of the SAPO solid related to the AFX-structure zeolite. This exchanged solid appears to have increased resistance to the presence of water.

Ogura et al. (Bull. Chem. Soc. Jpn. 2018, 91, 355-361) demonstrate the very good activity of a copper-exchanged SSZ-16 zeolite as compared with other zeolitic structures, even after hydrothermal aging.

WO 2017/080722 discloses a direct synthesis of a copper-containing zeolite. This synthesis requires starting from an FAU-structure zeolite and using a TEPA complexing agent and an $M(OH)_x$ element to obtain zeolites of various types, mainly of CHA type. Zeolites of ANA, ABW, PHI and GME type are also produced.

The applicant has discovered that a catalyst based on an intimate mixture of an AFX-structure zeolite and a BEA-structure zeolite, prepared in accordance with a particular synthesis method and at least one transition metal, in particular copper, demonstrated interesting results in terms of NO$_x$ conversion and selectivity to N$_2$O. In particular, the NOx conversion results, especially at low temperature (T<250° C.), are better than those obtained with prior art catalysts, such as catalysts based on copper-exchanged AFX-structure zeolite, while still retaining good selectivity to nitrous oxide N$_2$O.

SUMMARY OF THE INVENTION

The present invention relates to a process for preparing a catalyst comprising a mixture of AFX-structure and BEA-structure zeolites, and at least one transition metal, comprising at least the following steps:

i) mixing, in aqueous medium, of an FAU zeolite having an SiO$_2$/Al$_2$O$_3$ molar ratio of between 30 and 100 with at least one FAU-structure zeolite having an SiO$_2$/Al$_2$O$_3$ molar ratio of between 2 and 30 (upper limit excluded), and wherein the mathematical parameter, P$_{ze}$, corresponding to the mass percentage of the FAU zeolite with an SiO$_2$/Al$_2$O$_3$ molar ratio of between 30 and 100, in its anhydrous form (expressed in %) in the mixture of FAU zeolites, multiplied by the SiO$_2$/Al$_2$O$_3$ molar ratio of said same FAU zeolite with an SiO$_2$/Al$_2$O$_3$ molar ratio of between 30 and 100, is such that: 3250<P$_{ze}$<7200, of at least one nitrogenous organic compound R, chosen from 1,5-bis(methylpiperidinium)pentane dihydroxide, 1,6-bis(methylpiperidinium)hexane dihydroxide, 1,7-bis(methylpiperidinium)heptane dihydroxide, and mixtures thereof, and of at least one source of at least one alkali metal and/or alkaline-earth metal M of valence n, n being an integer greater than or equal to 1, the reaction mixture having the following molar composition:

(SiO$_2$ $_{(FAU)}$)/(Al$_2$O$_3$ $_{(FAU)}$) of between 30 and 80,
H$_2$O/(SiO$_2$ $_{(FAU)}$) of between 1 and 100,
R/(SiO$_2$ $_{(FAU)}$) of between 0.01 and 0.6,
M$_{2/n}$O/(SiO$_2$ $_{(FAU)}$) of between 0.005 and 0.45, wherein SiO$_2$ $_{(FAU)}$ is the molar amount of SiO$_2$ provided by all the FAU-structure zeolites introduced into the mixture, Al$_2$O$_3$ $_{(FAU)}$ is the molar amount of Al$_2$O$_3$ introduced by all the FAU-structure zeolites introduced into the mixture, H$_2$O the molar amount of water present in the reaction mixture, R the molar amount of said nitrogenous organic compound, M$_{2/n}$O being the molar amount of M$_{2/n}$O provided by all the FAU zeolites and by the source of alkali metal and/or alkaline-earth metal, until a precursor gel is obtained;

ii) hydrothermal treatment of said precursor gel obtained at the end of step i) at a temperature of between 120° C. and 220° C., for a period of between 12 hours and 15 days, to obtain a solid crystalline phase, termed "solid";

iii) at least one ion exchange comprising bringing the solid obtained at the end of the previous step into contact with at least one solution comprising at least one species that is capable of releasing a transition metal, in solution in reactive form, with stirring at ambient temperature for a period of between 1 hour and 2 days;

iv) heat treatment by drying the solid obtained at the end of the previous step at a temperature of between 20 and 150° C. for a period of between 2 and 24 hours, followed by calcination under a stream of air at a temperature of between 450 and 700° C. for a period of between 2 and 20 hours.

The present invention also relates to a catalyst comprising a mixture of a zeolite of AFX type and a zeolite of BEA type, and at least one transition metal, having a zeolite structure comprising:

between 30 and 90% by mass, preferably between 40 and 90% by mass of AFX-structure zeolite, relative to the total mass of said catalyst in its anhydrous form;

between 10 and 70% by mass, preferably between 10 and 60% by mass of BEA-structure zeolite, relative to the total mass of said catalyst in its anhydrous form;

wherein said transition metal is selected from the group made up of the following elements: Ti, V, Mn, Mo, Fe, Co, Cu, Cr, Zn, Nb, Ce, Zr, Rh, Pd, Pt, Au, W, Ag, preferably Cu, Fe, Nb, Ce, Mn, very preferably iron, copper or a mixture thereof, wherein the total content of transition metals is between 0.5 and 6% by mass, preferably between 0.5 and 5% by mass, and even more preferably between 1 and 4% by mass, relative to the total mass of the final catalyst, in its anhydrous form.

The present invention also relates to the use of the above catalyst or one prepared by the process described above, for the selective reduction of NO$_x$ by a reducing agent for the selective catalytic reduction of NOx, such as NH$_3$ or H$_2$.

The advantage of the present invention lies in the particular catalyst, based on a composite material containing an intimate mixture of an AFX-structure zeolite and a BEA-structure zeolite, and a transition metal, in particular copper. The catalyst according to the invention in fact exhibits improved properties compared to the catalysts of the prior art. In particular, the use of the catalyst according to the invention or prepared according to the process of the invention makes it possible to obtain lower initiation temperatures for the NOx conversion reaction and a better NOx conversion across the entire operating temperature range (150° C.-600° C.), while at the same time maintaining a good selectivity for N$_2$O.

DETAILED DESCRIPTION OF THE INVENTION

In accordance with the invention, a parameter P$_{ze}$ is defined for the FAU zeolites having an SiO$_2$/Al$_2$O$_3$ molar ratio of between 30 and 100 present in the starting mixture of FAU zeolites, as the mathematical product between the percentage by mass of the FAU zeolite with an SiO$_2$/Al$_2$O$_3$ molar ratio of between 30 and 100, in its anhydrous form (expressed in %) in the starting mixture of FAU zeolites, and its SiO$_2$/Al$_2$O$_3$ molar ratio, the sum of the percentages by mass of each of the FAU zeolites in the anhydrous form in the starting mixture being equal to 100. For example, when starting from a mixture of two FAU zeolites, said parameter P$_{ze}$ for the zeolite having an SiO$_2$/Al$_2$O$_3$ molar ratio of between 30 and 100 corresponds to the percentage (expressed in %) of said FAU zeolite having an SiO$_2$/Al$_2$O$_3$ molar ratio of between 30 and 100 in its anhydrous form in the starting mixture of FAU zeolites multiplied by the SiO$_2$/Al$_2$O$_3$ molar ratio of said FAU zeolite having an SiO$_2$/Al$_2$O$_3$ molar ratio of between 30 and 100.

According to the invention, the terms "gel" and "precursor gel" are synonymous and correspond to the homogeneous reaction mixture obtained at the end of step i) of the process according to the invention.

According to the present invention, the expression "between . . . and . . . " means that the values at the limits of the interval are included in the range of values which is described. Should this not be the case and should the values at the limits not be included in the range described, such a clarification will be given by the present invention.

The present invention relates in particular to a process for preparing a catalyst comprising a mixture of AFX-structure and BEA-structure zeolites, and at least one transition metal, comprising at least the following steps:

i) mixing, in aqueous medium, of an FAU zeolite having an $SiO_2/Al_2O_3$ molar ratio of between 30 and 100 with at least one FAU-structure zeolite having an $SiO_2/Al_2O_3$ molar ratio of between 2 and 30 (upper limit excluded), and wherein the mathematical parameter, $P_{ze}$, corresponding to the mass percentage of the FAU zeolite with an $SiO_2/Al_2O_3$ molar ratio of between 30 and 100, in its anhydrous form (expressed in %) in the mixture of FAU zeolites, multiplied by the $SiO_2/Al_2O_3$ molar ratio of said same FAU zeolite with an $SiO_2/Al_2O_3$ molar ratio of between 30 and 100, is such that: $3250<P_{ze}<7200$, preferably $3350<P_{ze}<7100$, of at least one nitrogenous organic compound R, chosen from 1,5-bis (methylpiperidinium)pentane dihydroxide, 1,6-bis(methylpiperidinium)hexane dihydroxide, 1,7-bis(methylpiperidinium)heptane dihydroxide, and mixtures thereof, and of at least one source of at least one alkali metal and/or alkaline-earth metal M of valence n, n being an integer greater than or equal to 1, the reaction mixture having the following molar composition:

$(SO_{2\ (FAU)})/(Al_2O_{3\ (FAU)})$ between 30 and 80, preferably between 32 and 70

$H_2O/(SiO_{2\ (FAU)})$ between 1 and 100, preferably between 5 and 60

$R/(SiO_{2\ (FAU)})$ between 0.01 and 0.6, preferably between 0.05 and 0.5

$M_{2/n}O/(SiO_{2\ (FAU)})$ between 0.005 and 0.45, preferably between 0.01 and 0.25 wherein $SiO_2$ (FAU) is the molar amount of $SiO_2$ provided by all the FAU-structure zeolites introduced into the mixture, $Al_2O_{3\ (FAU)}$ is the molar amount of $Al_2O_3$ introduced by all the FAU-structure zeolites introduced into the mixture, $H_2O$ the molar amount of water present in the reaction mixture, R the molar amount of said nitrogenous organic compound, $M_{2/n}O$ being the molar amount of $M_{2/n}O$ provided by all the FAU zeolites and by the source of alkali metal and/or alkaline-earth metal, until a precursor gel is obtained;

ii) hydrothermal treatment of said precursor gel obtained at the end of step i) at a temperature of between 120° C. and 220° C., for a period of between 12 hours and 15 days, to obtain a solid crystalline phase, termed "solid";

iii) at least one ion exchange comprising bringing said solid obtained at the end of the previous step into contact with at least one solution comprising at least one species that is capable of releasing a transition metal, in particular copper, in solution in reactive form, with stirring at ambient temperature for a period of between 1 hour and 2 days;

iv) heat treatment by drying the solid obtained at the end of the previous step at a temperature of between 20 and 150° C. for a period of between 2 and 24 hours, followed by calcination under a stream of air at a temperature of between 450 and 700° C. for a period of between 2 and 20 hours;

it being possible advantageously to reverse steps iii) and iv), and optionally to repeat them if necessary.

The present invention also relates to the catalyst comprising a mixture of AFX-structure and BEA-structure zeolites and at least one transition metal, advantageously which is capable of being obtained or which is directly obtained by the process described above.

Finally, the invention relates to the use of a catalyst according to the invention for the selective catalytic reduction of NOx in the presence of a reducing agent.

The Catalyst

The catalyst according to the invention comprises at least a mixture of a zeolite of AFX type and a zeolite of BEA type, and at least one additional transition metal, preferably copper.

The catalyst according to the invention has a zeolite structure comprising:

between 30 and 90% by mass, preferably between 40 and 90% by mass of AFX-structure zeolite, relative to the total mass of said catalyst in its anhydrous form;

between 10 and 70% by mass, preferably between 10 and 60% by mass of BEA-structure zeolite, relative to the total mass of said catalyst in its anhydrous form.

Preferably, the mass ratio (AFX/BEA) of the AFX zeolite relative to the BEA zeolite, in the catalyst according to the invention, is between 0.4 and 9, preferentially between 0.5 and 7.5 and even more preferentially between 1 and 4.

Advantageously, the BEA-structure zeolite of the catalyst according to the invention is preferably a beta zeolite containing a mixture containing between 35 and 45% by mass, preferably 40% by mass, of polymorph A and between 55 and 65% by mass, preferably 60% by mass, of polymorph B.

The catalyst according to the invention advantageously has an $SiO_2/Al_2O_3$ molar ratio of between 2 and 100, preferably between 4 and 90 and more preferentially between 6 and 80.

According to the invention, the terms "composite material", "zeolite composite material" and "composite aluminosilicate material" are synonyms and are used interchangeably to denote the solid material composed of an intimate mixture of AFX-structure and BEA-structure zeolites. The composite material of the catalyst according to the invention is advantageously obtained by direct synthesis, that is to say in a single reaction step, at the end of step ii) of the preparation process according to the invention. The composite aluminosilicate material, containing an intimate mixture of AFX and BEA zeolites, does not result from simple mechanical mixing of at least one AFX-structure zeolite and at least one BEA-structure zeolite.

According to the invention, the transition metal(s) contained in the catalyst is (are) selected from the elements of the group formed by the elements from Groups 3 to 12 of the Periodic Table of Elements, including lanthanides. In particular, the transition metal(s) contained in the catalyst is (are) selected from the group made up of the following elements: Ti, V, Mn, Mo, Fe, Co, Cu, Cr, Zn, Nb, Ce, Zr, Rh, Pd, Pt, Au, W, Ag.

Preferably, the catalyst according to the invention comprises copper, alone or in combination with at least one other transition metal, chosen from the group of elements listed above; in particular Fe, Nb, Ce, Mn. Preferably, the transition metal is iron, copper or a mixture thereof.

According to the invention, the total content of transition metals is between 0.5 and 6% by mass, preferably between 0.5 and 5% by mass, and even more preferably between 1 and 4% by mass, relative to the total mass of the final catalyst, in its anhydrous form.

Advantageously, the catalyst defined above is capable of being obtained or is directly obtained by the preparation process according to the invention and described below.

According to one embodiment of the invention, the catalyst contains only copper as transition metal, the copper content by mass being between 0.5 and 6%, preferably between 0.5 and 5%, preferably between 1 and 4% and even more preferably between 1.5 and 3.5% relative to the total mass of the final catalyst in its anhydrous form.

According to another embodiment of the invention, the catalyst comprises copper and another transition metal, preferably Fe, Nb, Ce, Mn. In this embodiment, the copper content of the catalyst is between 0.05 and 2% by mass, preferably between 0.5 and 2% by mass, while that of the other transition metal is preferably between 1 and 4% by mass, the transition metal contents being given as percentages by mass relative to the total mass of the final catalyst in its anhydrous form.

According to a third embodiment of the invention, the catalyst contains only iron as transition metal, the iron content by mass being between 0.5 and 5%, preferably between 1 and 4% and preferably between 1.5 and 3.5% relative to the total mass of the final catalyst in its anhydrous form.

According to another particular embodiment of the invention, the catalyst comprises iron and another transition metal, preferably Cu, Nb, Ce, Mn. In this embodiment, the iron content of the catalyst is between 0.05 and 2% by mass, preferably between 0.5 and 2% by mass, while that of the other transition metal is preferably between 1 and 4% by mass, the transition metal contents being given as percentages by mass relative to the total mass of the final catalyst in its anhydrous form.

The catalyst according to the invention may also contain other elements, such as for example alkali and/or alkaline-earth metals, for example sodium, originating in particular from the synthesis, in particular of the compounds of the reaction medium of step i) of the process for preparing said catalyst.

Process for Preparing the Catalyst

Mixing Step i)

The preparation process according to the invention comprises a step i) of mixing, in aqueous medium, an FAU zeolite having an $SiO_2/Al_2O_3$ molar ratio of between 30 and 100, with at least one FAU-structure zeolite having an $SiO_2/Al_2O_3$ molar ratio of between 2 and 30 (upper limit excluded), and wherein $3250<P_{ze}<7200$, preferably $3350<P_{ze}<7100$, of at least one nitrogenous organic compound R chosen from 1,5-bis(methylpiperidinium)pentane dihydroxide, 1,6-bis(methylpiperidinium)hexane dihydroxide, 1,7-bis(methylpiperidinium)heptane dihydroxide and mixtures thereof, and of at least one source of at least one alkali metal and/or alkaline-earth metal M of valence n, n being an integer greater than or equal to 1, the reaction mixture having the following molar composition:

$(SiO_{2\ (FAU)})/(Al_2O_{3\ (FAU)})$ between 30 and 80, preferably between 32 and 70

$H_2O/(SiO_{2\ (FAU)})$ between 1 and 100, preferably between 5 and 60

$R/(SiO_{2\ (FAU)})$ of between 0.01 and 0.6, preferably between 0.05 and 0.5

$M_{2/n}O/(SiO_{2\ (FAU)})$ of between 0.005 and 0.45, preferably between 0.01 and 0.25 wherein $SiO_{2\ (FAU)}$ is the molar amount of $SiO_2$ provided by all the FAU-structure zeolites introduced into the mixture, $Al_2O_{3\ (FAU)}$ is the molar amount of $Al_2O_3$ introduced by all the FAU-structure zeolites introduced into the mixture, $H_2O$ the molar amount of water present in the reaction mixture, R the molar amount of said nitrogenous organic compound, $M_{2/n}O$ being the molar amount of $M_{2/n}O$ provided by all the FAU zeolites and by the source of alkali metal and/or alkaline-earth metal.

Step i) makes it possible to obtain a homogeneous precursor gel.

In accordance with the invention, an FAU zeolite having an $SiO_2/Al_2O_3$ molar ratio of between 30 (lower limit included) and 100 (upper limit included) and at least one FAU-structure zeolite having an $SiO_2/Al_2O_3$ molar ratio of between 2 (lower limit included) and 30 (upper limit excluded) are incorporated into the reaction mixture for the implementation of step (i) as sources of silicon and aluminum element. The $SiO_2/Al_2O_3$ molar ratios of the FAU zeolites incorporated into the reaction mixture in step i) of the process according to the invention are advantageously different from one another. Advantageously, the overall molar ratio of the silicon element, expressed in oxide form $SiO_2$, provided by all the starting FAU zeolites, relative to the aluminum element, expressed in oxide form $Al_2O_3$, provided by all the starting FAU zeolites, is between 30 and 80, preferably between 32 and 70.

In accordance with the invention, the FAU-structure zeolites used in the reaction mixture in step i) of the process according to the invention have different $SiO_2/Al_2O_3$ molar ratios and are such that: $3250<P_{ze}<7200$, preferably $3350<P_{ze}<7100$.

Thus, depending on the starting FAU zeolites, the $SiO_2/Al_2O_3$ molar ratios of which are different, and on their relative amounts, the $SiO_2/Al_2O_3$ molar ratio of the precursor gel of the targeted AFX-BEA composite material can be adjusted.

The starting FAU-structure zeolites, that with an $SiO_2/Al_2O_3$ molar ratio of between 30 and 100 and that or those with an $SiO_2/Al_2O_3$ molar ratio of between 2 and 30 (upper limit excluded), can be obtained by any method known to those skilled in the art, such as for example by direct synthesis in the case of FAU zeolites having an $SiO_2/Al_2O_3$ molar ratio of less than 6, or by steam treatment (steaming) and/or acid washes on an FAU-structure zeolite having an $SiO_2/Al_2O_3$ molar ratio of less than 6 in the case of FAU zeolites having an $SiO_2/Al_2O_3$ molar ratio of greater than or equal to 6. Said starting FAU-structure zeolites can be used in their sodium form or any other form. They may for example, before being used in the process according to the invention, undergo an exchange of part or all of their sodium cations with ammonium cations, optionally followed by a calcining step. Among the sources of FAU zeolites with an $SiO_2/Al_2O_3$ molar ratio of between 30 and 100 and the sources of FAU zeolites with an $SiO_2/Al_2O_3$ molar ratio of between 2 and 30 (upper limit excluded) mention may be made of the commercial zeolites of Y type produced by Zeolyst and by Tosoh, for example the commercial zeolites CBV100, CBV600, CBV712, CBV720, CBV760 and CBV780, and the commercial zeolites HSZ-320HOA, HSZ-350HUA, HSZ-360HUA and HSZ-385HUA.

In accordance with the invention, the mixing step i) is carried out in an aqueous medium, that is to say in water, preferably deionized water, such that the $H_2O/(SiO_{2\ (FAU)})$ molar ratio is advantageously between 1 and 100, preferably between 5 and 60, $SiO_{2\ (FAU)}$ being the molar amount of $SiO_2$ provided by the starting FAU zeolite, $H_2O$ being the molar amount of water present in the reaction mixture.

In accordance with the invention, the reaction mixture comprises at least one, preferably one, nitrogenous organic compound R chosen from 1,5-bis(methylpiperidinium)pentane dihydroxide, 1,6-bis(methylpiperidinium)hexane dihydroxide, 1,7-bis(methylpiperidinium)heptane dihydroxide and mixtures thereof, said compound being incorporated into the reaction mixture for carrying out step (i), as an organic structuring agent. Preferably, the structuring agent R incorporated into the reaction mixture is 1,6-bis(methylpiperidinium)hexane dihydroxide. The anion associated with the quaternary ammonium cations present in the organic structuring species for the synthesis of an AFX-BEA zeolite composite material according to the invention is the hydroxide anion.

Advantageously, the structuring agent R is incorporated into the reaction mixture such that the $(R/(SiO_{2\ (FAU)}))$ molar ratio between the molar amount of said nitrogenous organic compound R and the molar amount of $SiO_2$ provided by all the starting zeolites is between 0.01 and 0.6, preferably between 0.05 and 0.5.

According to the invention, at least one source of at least one alkali metal and/or alkaline-earth metal M of valence n, n being an integer greater than or equal to 1, is used in the reaction mixture of step i). The alkali metal and/or alkaline-earth metal M is preferably chosen from lithium, potassium, sodium, magnesium and calcium and the mixture of at least two of these metals. Very preferably, M is sodium. The source of at least one alkali metal and/or alkaline-earth metal M is preferably sodium hydroxide.

Advantageously, the amount of alkali metal and/or alkaline-earth metal M of valence n incorporated into the reaction mixture is such that the $M_{2/n}O/(SiO_{2\ (FAU)})$ molar ratio is between 0.005 and 0.45, preferably between 0.01 and 0.25, $M_{2/n}O$ being the molar amount of $M_{2/n}O$ provided by all the FAU zeolites and by the source of alkali metal and/or alkaline-earth metal, and $SiO_{2\ (FAU)}$ the molar amount of $SiO_2$ provided by all the FAU zeolites incorporated into the reaction mixture.

The mixing step i) of the process according to the invention is carried out until a homogeneous reaction mixture is obtained, called a gel or precursor gel, preferably for a period greater than or equal to 10 minutes and advantageously for less than 2 hours, in particular less than 1.5 hours, preferably at ambient temperature and preferably with stirring, at low or high shear rate, the stirring system being any system known to those skilled in the art, for example a mechanical stirrer with blades or a turbine.

During this mixing step i), the aqueous solvent introduced may optionally partly evaporate.

Step (i) of the process according to the invention consists in preparing an aqueous reaction mixture containing at least two FAU-structure zeolites, at least one nitrogenous organic compound R, R being 1,5-bis(methylpiperidinium)pentane dihydroxide, 1,6-bis(methylpiperidinium)hexane dihydroxide and/or 1,7-bis(methylpiperidinium)heptane dihydroxide in the presence of at least one source of one or more alkali metal(s) and/or alkaline-earth metal(s), to obtain a precursor gel of an AFX-BEA composite material. The amounts of said reagents are adjusted as indicated above so as to give this gel a composition allowing an AFX-BEA composite material to be crystallized.

It may be advantageous to add seeds of an AFX-structure zeolite, of a BEA-structure zeolite and/or of an AFX-BEA composite material to the reaction mixture during said step i) of the process of the invention in order to reduce the time required for the formation of crystals of the zeolite composite material and/or the total crystallization time. Said seed crystals also promote the formation of said AFX-BEA composite material to the detriment of impurities. The seed crystals are generally added in a proportion of between 0.01% and 10% of the total mass of the sources of said tetravalent and trivalent element(s) considered in their anhydrous form used in the reaction mixture, said seed crystals not being taken into account in the total mass of the sources of the tetravalent and trivalent elements. Said seeds are not taken into account either for determining the composition of the reaction mixture and/or of the gel, defined above, i.e. in the determination of the various molar ratios of the composition of the reaction mixture.

It may be advantageous to perform a maturation of the reaction mixture during said step i) of the process of the invention, before the hydrothermal crystallization, so as to control the size of the crystals of an AFX-BEA zeolite composite material. Said maturation also promotes the formation of said AFX-BEA zeolite composite material to the detriment of impurities. The maturation of the reaction mixture during said step i) of the process of the invention may be performed at ambient temperature or at a temperature of between 20 and 100° C. with or without stirring, for a period advantageously of between 30 minutes and 48 hours.

Hydrothermal Treatment Step ii)

The preparation process according to the invention comprises a step ii) of hydrothermal treatment of said precursor gel obtained at the end of step i), which has optionally been matured, at a temperature of between 120° C. and 220° C., preferably between 150° C. and 195° C., for a period of between 12 hours and 15 days, preferably between 12 hours and 12 days and more preferably between 12 hours and 8 days. Advantageously, the hydrothermal treatment is carried out under an autogenous reaction pressure, optionally by adding gas, for example nitrogen.

The hydrothermal treatment is generally performed with or without stirring, preferably with stirring. Any stirring system known to those skilled in the art can be used, for example inclined blades with counter-blades, stirring turbo-mixers, Archimedean screws.

These operating conditions make it possible to obtain crystallization, preferably complete crystallization, of the targeted composite material. Crystallization is considered complete as soon as no more presence of amorphous product or FAU zeolite is detected by XRD analysis of a sample of the reaction medium extracted during the synthesis. According to the invention, this hydrothermal treatment step ii) can also be called a crystallization step, a reaction step or else a synthesis step. The crystallized solid phase obtained is said to be "solid".

At the end of the reaction, the solid phase formed is advantageously filtered, washed, preferably with water, preferably deionized water, and then preferably dried. The drying is generally performed at a temperature of between 20° C. and 150° C., preferably between 60° C. and 100° C., for a period of between 5 and 24 hours.

The loss on ignition (LOI) of said solid obtained after drying (when the latter is carried out at the end of step ii)) is generally between 4 and 15% by weight. According to the invention, the loss on ignition of a sample, referred to by the acronym LOI, corresponds to the difference in the mass of the sample tested before and after a heat treatment at 1000° C. for 2 hours. It is expressed in % corresponding to the percentage loss of mass. The loss on ignition corresponds in general to the loss of solvent (such as water) contained in the solid, but also to the removal of organic compounds contained in the inorganic solid constituents.

Exchange Step iii)

Advantageously, the process for preparing the catalyst according to the invention includes at least one ion-exchange step which comprises bringing the solid obtained at the end of the previous step, i.e. the composite aluminosilicate material obtained at the end of step ii) or the dried and calcined composite aluminosilicate material obtained at the end of step iv) in the case where steps iii) and iv) are reversed, into contact with at least one solution comprising at least one species capable of releasing a transition metal, preferably copper, in solution in reactive form, preferably with stirring, at ambient temperature for a period of between 1 hour and 2 days, advantageously for a period of between 0.5 day and 1.5 days, the concentration of said species capable of releasing the transition metal in said solution depending on the amount of transition metal to be incorporated into said crystalline solid or said dried and calcined crystalline solid. Preferably, the ion-exchange step iii) of the preparation process according to the invention is carried out at the end of the hydrothermal treatment step ii).

It is also advantageous to obtain the protonated form of the composite aluminosilicate material after step ii). Said hydrogen form may be obtained by performing an ion exchange with an acid, in particular a strong mineral acid such as hydrochloric, sulfuric or nitric acid, or with a compound such as ammonium chloride, sulfate or nitrate, before the ion exchange with the transition metal(s).

The transition metal released in the exchange solution is selected from the group made up of the following elements: Ti, V, Mn, Mo, Fe, Co, Cu, Cr, Zn, Nb, Ce, Zr, Rh, Pd, Pt, Au, W, Ag. Preferably the transition metal is Fe, Cu, Nb, Ce or Mn, preferentially Fe or Cu and even more preferably Cu.

According to the invention, "species capable of releasing a transition metal" is understood to mean a species that is capable of dissociating in an aqueous medium, such as for example sulfates, nitrates, chlorides, oxalates, organometallic complexes of a transition metal, or mixtures thereof. Preferably, the species capable of releasing a transition metal is a sulfate or a nitrate of said transition metal.

According to the invention, the solution with which the crystalline solid or dried and calcined crystalline solid is brought into contact comprises at least one species capable of releasing a transition metal, preferably a species capable of releasing a transition metal, preferably copper.

Advantageously, the process for preparing the catalyst according to the invention comprises a step iii) of ion exchanges by bringing the crystalline solid (that is to say the solid obtained at the end of step ii)), or the dried and calcined crystalline solid (that is to say the solid obtained at the end of step iv) in the case where steps iii) and iv) are reversed) into contact with a solution comprising at least one species, preferably a single species, capable of releasing a transition metal, or by successively bringing said solid into contact with several solutions, each comprising at least one species, preferably one species, capable of releasing a transition metal, the different solutions advantageously comprising different species able to release a transition metal.

According to the invention, the solution with which the crystalline solid is brought into contact comprises at least one species capable of releasing a transition metal, preferably just one species capable of releasing a transition metal, preferably iron or copper, preferentially copper.

At the end of the exchange, the solid obtained is advantageously filtered, washed, for example with deionized water, and, preferably, then dried to obtain a powder. In the case where step iii) comprises successively bringing the solid into contact with different solutions, the solid obtained after each contacting can be advantageously filtered, washed, for example with deionized water, then, preferably, dried. The drying is generally performed at a temperature of between 20° C. and 150° C., preferably between 60° C. and 100° C., for a period of between 5 and 24 hours.

The total amount of transition metal, preferably copper, contained in said final catalyst is between 0.5 and 6% by mass, preferably between 0.5 and 5% by mass, and even more preferably between 1 and 4% by mass, relative to the total mass of the catalyst in its anhydrous form.

According to one embodiment of the invention wherein the catalyst contains only copper as transition metal, the content by mass of copper incorporated into the catalyst is between 0.5 and 6%, preferably between 0.5 and 5%, preferably between 1 and 4% and even more preferably between 1.5 and 3.5% relative to the total mass of the final catalyst in its anhydrous form.

According to another embodiment of the invention wherein the catalyst comprises copper and another transition metal, preferably Fe, Nb, Ce, Mn, the copper content of the catalyst obtained is between 0.05 and 2% by mass, preferably between 0.5 and 2% by mass, while that of the other transition metal is preferably between 1 and 4% by mass, the transition metal contents being given as percentages by mass relative to the total mass of the final catalyst in its anhydrous form. In this embodiment, the exchange step iii) is preferably carried out by successively bringing into contact two solutions, one of which contains a species capable of releasing copper in solution and the other solution of which contains a species capable of releasing a transition metal other than copper, preferably Fe, Nb, Ce, Mn.

According to a third embodiment of the invention wherein the catalyst contains only iron as transition metal, the iron content by mass is between 0.5 and 5%, preferably between 1 and 4% and preferably between 1.5 and 3.5% relative to the total mass of the final catalyst in its anhydrous form.

According to another particular embodiment of the invention wherein the catalyst comprises iron and another transition metal, preferably Cu, Nb, Ce, Mn, the iron content of the catalyst obtained is between 0.05 and 2% by mass, preferably between 0.5 and 2% by mass, while that of the other transition metal is preferably between 1 and 4% by mass, the transition metal contents being given as percentages by mass relative to the total mass of the final catalyst in its anhydrous form. In this embodiment, the exchange step iii) is advantageously carried out by successively bringing into contact two solutions, one of which contains a species capable of releasing iron in solution and the other solution of which contains a species capable of releasing a transition metal other than copper, preferably Cu, Nb, Ce, Mn.

Heat Treatment Step iv)

The preparation process according to the invention includes a step iv) of heat treatment performed at the end of the previous step, i.e. at the end of the hydrothermal treatment step ii) or at the end of the exchange step iii), preferably at the end of the ion-exchange step iii). According to the invention, the two steps iii) and iv) can advantageously be reversed and also optionally be repeated. Each of the two steps iii) and iv) can also optionally be repeated individually.

Said heat treatment step iv) comprises drying the solid at a temperature of between 20 and 150° C., preferably between 60 and 100° C., for a period of between 2 and 24 hours, followed by calcining, corresponding to a treatment by combustion in air, which is optionally dry, at a temperature of between 450 and 700° C., preferably between 500 and 600° C. for a period of between 2 and 20 hours, preferably between 5 and 10 hours, preferentially between 6 and 9 hours, the flow rate of optionally dry air preferably being between 0.5 and 1.5 l/h/g of solid to be treated, preferentially between 0.7 and 1.2 l/h/g of solid to be treated. The calcination may be preceded by a gradual temperature increase.

In particular, the catalyst obtained by a process comprising at least steps i), ii), iii) and iv) as described above has improved $NO_x$ conversion properties.

Characterization of the Catalyst Prepared According to the Invention

The catalyst according to the invention comprises a zeolite structure composed of a mixture of AFX-structure and BEA-structure zeolites according to the classification of the International Zeolite Association (IZA), exchanged with at least one transition metal. This structure is characterized by X-ray diffraction (XRD).

The X-ray diffraction technique also makes it possible to determine the mass proportion of the mixture of AFX and BEA zeolites in said catalyst and the relative proportions of each zeolite, AFX and BEA. Advantageously, the overall proportion by mass of the AFX and BEA zeolites in the catalyst obtained is greater than or equal to 90%, preferably greater than or equal to 95%, preferentially greater than or equal to 99% and even more preferably greater than or equal to 99.8%, relative to the total mass of said catalyst, in its anhydrous form. In other words, the catalyst obtained comprises less than 10% by mass, preferably less than 5% by mass, preferentially less than 1% by mass and even more preferably less than 0.2% by mass of impurities and/or of crystalline or amorphous phase other than AFX and BEA (the limits not being included). Very advantageously, the process of the invention leads to the formation of a catalyst comprising a zeolite structure composed of a mixture of AFX and BEA zeolites, free of any other crystalline or amorphous phase and/or any impurity.

The X-ray diffraction (XRD) pattern is obtained by radiocrystallographic analysis by means of a diffractometer using the conventional powder method with Kai radiation of copper ($\lambda$=1.5406 Å). On the basis of the position of the diffraction peaks represented by the angle 2$\theta$, the lattice constant distances $d_{hkl}$ characteristic of the sample are calculated using the Bragg relationship. The measurement error $\Delta(d_{hkl})$ on $d_{hkl}$ is calculated by virtue of the Bragg relationship as a function of the absolute error $\Delta(2\theta)$ assigned to the measurement of 2$\theta$. An absolute error $\Delta(2\theta)$ equal to ±0.02° is commonly accepted. The relative intensity $I_{rel}$ assigned to each value of $d_{hkl}$ is measured according to the height of the corresponding diffraction peak. Comparison of the diffraction pattern with the ICDD (International Center for Diffraction Data) database sheets using software such as for example DIFFRACT.SUITE also makes it possible to identify the crystalline phases present in the material obtained.

The X-ray diffraction pattern of the AFX-BEA composite material obtained at the end of step ii) of the process according to the invention, or of the catalyst according to the invention, advantageously obtained at the end of step iv) of the process of the invention, comprises at least the lines at the values of $d_{hkl}$ given in Table 1. In the column of the $d_{hkl}$ values, the mean values of the inter-lattice distances in Angstöms (Å) are given. Each of these values must be assigned the measurement error $\Delta(d_{hkl})$ of between ±0.6 Å and ±0.01 Å.

TABLE 1

Mean values of the $d_{hkl}$ values and relative intensities measured on an X-ray diffraction pattern of the catalyst according to the invention or of the composite material obtained at the end of step ii) of the process according to the invention

| 2 theta (°) | dhkl (Å) | Irel | 2 theta (°) | dhkl (Å) | Irel |
|---|---|---|---|---|---|
| 7.49 | 11.79 | vw-w | 26.11 | 3.41 | w-m |
| 7.71 | 11.46 | vw-w | 26.94 | 3.31 | vw |
| 8.71 | 10.14 | mw-m | 27.11 | 3.29 | vw |
| 11.66 | 7.59 | w-mw | 27.61 | 3.23 | vw |
| 12.97 | 6.82 | w | 28.04 | 3.18 | mw-m |
| 15.00 | 5.90 | vw | 28.68 | 3.11 | vw |
| 15.40 | 5.75 | vw | 29.51 | 3.03 | vw |
| 15.66 | 5.66 | w-mw | 30.19 | 2.96 | vw-w |
| 17.47 | 5.07 | mw | 30.58 | 2.92 | mw |
| 17.90 | 4.95 | w-mw | 30.99 | 2.88 | vw |
| 19.42 | 4.57 | vw | 31.59 | 2.83 | w-mw |
| 19.88 | 4.46 | vw-w | 32.50 | 2.75 | vw |
| 20.38 | 4.36 | S-VS | 33.73 | 2.66 | w-mw |
| 21.08 | 4.21 | w | 34.29 | 2.61 | vw |
| 21.31 | 4.17 | vw-w | 34.78 | 2.58 | vw |
| 21.82 | 4.07 | S-VS | 35.11 | 2.55 | vw |
| 22.19 | 4.00 | w-m | 35.79 | 2.51 | vw |
| 22.34 | 3.98 | w-VS | 37.56 | 2.39 | vw |
| 22.54 | 3.94 | vw-w | 38.00 | 2.37 | vw |
| 22.70 | 3.91 | vw-w | 39.18 | 2.30 | vw |
| 23.67 | 3.76 | mw | 39.61 | 2.30 | vw |
| 25.24 | 3.52 | vw | | | | where VS = very strong; S = strong; m = medium; mw = moderately weak; w = weak; vw = very weak. The relative intensity $I_{rel}$ is given in relation to a relative intensity scale in which a value of 100 is assigned to the most intense line of the X-ray diffraction pattern: vw < 15; 15 ≤ w < 30; 30 ≤ mw < 50; 50 ≤ m < 65; 65 ≤ S < 85; VS ≥ 85; 1 ≤ vw-w < 30; 30 ≤ mw-m < 65; 15 ≤ w-mw < 50; 65 ≤ S-VS ≤ 100; 15 ≤ w-m < 65; 15 ≤ w-VS ≤ 100.

According to the invention, the mass composition of the catalyst, in particular the relative mass fractions of the AFX-structure and BEA-structure zeolites present in said catalyst, is advantageously determined using a method similar to standard ASTM D3906 03, by comparison of the areas of the peaks at the angles (2$\theta$) 20.38±0.1 (hkl: 211); 23.67±0.1 (hkl: 105); 26.1±0.1 (hkl: 303) and 28.02±0.1 (hkl: 106) of the X-ray diagrams obtained for the composite material according to the invention and an AFX-structure reference zeolite, preferably of high purity, advantageously having a purity greater than or equal to 99.8%. The mass ratio of the two zeolites AFX and BEA in the composite material according to the invention is thus evaluated by comparing the sum of the areas of the peaks at the angles (2$\theta$) mentioned above obtained for the composite material prepared according to the invention, with that obtained for an AFX zeolite reference sample and by using the following calculation formula:

$$AFX/BEA = SAFXc/(SAFXr - SAFXc)$$

wherein SAFXc is the sum of the areas of the peaks present at the angles (2$\theta$) 20.38±0.1 (hkl: 211); 23.67±0.1 (hkl: 105); 26.1±0.1 (hkl: 303) and 28.02±0.1 (hkl: 106) of the diffractogram of the AFX-BEA composite material containing copper, prepared according to the invention, and SAFXr is the sum of the areas of the peaks present at the angles (2$\theta$): 20.38 (hkl: 211); 23.67 (hkl: 105); 26.1 (hkl: 303) and 28.02 (hkl: 106) of the diffractogram of the pure AFX-structure zeolite, used as a reference.

The qualitative and quantitative analysis of the chemical species present in the materials obtained is carried out by X-ray fluorescence (XRF) spectrometry. This is a technique of chemical analysis using a physical property of matter, the X-ray fluorescence. The spectrum of X-rays emitted by the material is characteristic of the composition of the sample; by analyzing this spectrum, it is possible to deduce therefrom the elemental composition, that is to say the mass concentrations of elements.

The loss on ignition (LOI) of the catalyst obtained after the drying step (and before calcination) or after the calcination step of step iv) of the process according to the invention is generally between 2 and 15% by weight, preferably between 4 and 15% by weight. The loss on ignition of a catalyst sample, referred to by the acronym LOI, corresponds to the difference in mass of the sample before and after a heat treatment at 1000° C. for 2 hours. It is expressed in % corresponding to the percentage loss of mass. The loss on ignition corresponds in general to the loss of solvent (such as water) contained in the solid, but also to the removal of organic compounds contained in the inorganic solid constituents.

Use of the Catalyst According to the Invention

The invention also relates to the use of the catalyst according to the invention, advantageously directly prepared or capable of being prepared by the process described above, for the selective reduction of $NO_x$ by a reducing agent such as $NH_3$ or Hz, advantageously formed by deposition in the form of a coating (or "washcoat") on a monolith (or structure), preferably a honeycomb structure, primarily for mobile applications, or a plate structure, as found in particular for stationary applications.

The honeycomb structure is formed of parallel channels open at both ends ("flow-through channels") or comprises porous filtering walls, in which case the adjacent parallel channels are alternately blocked at both ends of the channels to force the gas flow to pass through the wall ("wall-flow monolith"). Said honeycomb structure thus coated constitutes a catalytic block. Said structure may be composed of cordierite, silicon carbide (SiC), aluminum titanate (AlTi), alpha-alumina, mullite, or any other material of which the porosity is between 30 and 70%. Said structure may be created in metal sheet, in stainless steel containing chromium and aluminum (FeCrAl steel).

The amount of catalyst according to the invention that is deposited on said honeycomb structure is between 50 and 180 g/l for the filtering structures and between 80 and 200 g/l for the structures with open channels.

The catalyst according to the invention is advantageously combined with a binder such as cerine, zirconium oxide, alumina, non-zeolitic silica-alumina, titanium oxide, a cerine-zirconia mixed oxide, a tungsten oxide or a spinel in order to be formed by deposition in the form of a coating. Said coating is advantageously applied to a monolithic structure, or monolith, very preferably to a honeycomb structure, by a deposition method known as washcoating, which involves soaking the monolith in a suspension (or slurry) of powdered catalyst according to the invention in a solvent, preferably water, and optionally binders, metal oxides, stabilizers or other promoters. This soaking step may be repeated until the desired amount of coating is obtained. In certain cases the slurry may also be sprayed inside the monolith. Once the coating has been deposited, the monolith is calcined at a temperature of 300 to 600° C. for 1 to 10 hours.

Said monolithic structure may be coated with one or more coatings. The coating comprising the catalyst according to the invention is advantageously combined with, i.e. covers or is covered by, another coating having the capacity to adsorb pollutants, in particular NOx, to reduce pollutants, in particular NOx, or to promote the oxidation of pollutants, in particular that of ammonia.

Another possibility is for the catalyst to be in the form of an extrudate. In this case, the structure obtained may contain up to 100% of catalyst according to the invention.

Said structure coated with the catalyst according to the invention or obtained by extrusion of the catalyst according to the invention is advantageously integrated into an exhaust line of an internal combustion engine operating mainly in lean-mixture mode, that is to say with excess air relative to the stoichiometry of the combustion reaction, as is the case with diesel engines for example. Under these engine operating conditions, the exhaust gases contain in particular the following pollutants: soot, unburned hydrocarbons (HCs), carbon monoxide (CO), nitrogen oxides (NOx). Upstream of said structure coated with the catalyst according to the invention may be placed an oxidation catalyst, the function of which is to oxidize HCs and CO, and a filter for removing soot from the exhaust gases, the function of said coated structure being to remove the NOx, its operating range being between 100 and 900° C. and preferably between 200° C. and 500° C.

LIST OF FIGURES

Figure 1:
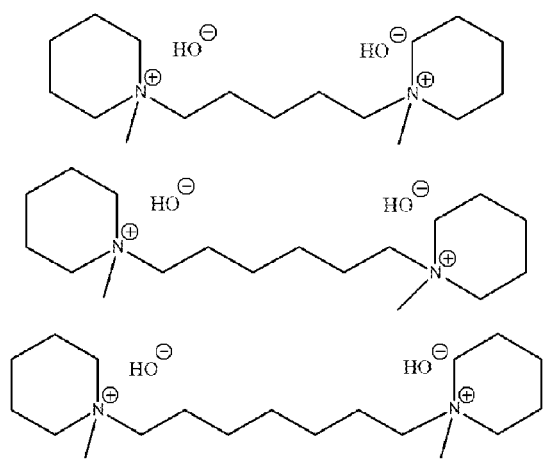
FIG. 1 represents the chemical formulae of the nitrogenous organic compounds which may be chosen as the structuring agent used in the synthesis process according to the invention.

The invention is illustrated by the examples that follow, which are not in any way limiting in nature.

EXAMPLES

Example 1: Preparation of 1,6-bis(methylpiperidinium)hexane dihydroxide (Structuring Agent R)

50 g of 1,6-dibromohexane (0.20 mol, 99%, Alfa Aesar) are placed in a 1 l round-bottomed flask containing 50 g of N-methylpiperidine (0.51 mol, 99%, Alfa Aesar) and 200 ml of ethanol. The reaction medium is stirred at reflux for 5 hours. The mixture is then cooled to ambient temperature and then filtered. The mixture is poured into 300 ml of cold diethyl ether and the precipitate formed is filtered off and washed with 100 ml of diethyl ether. The solid obtained is recrystallized in an ethanol/ether mixture. The solid obtained is dried under vacuum for 12 hours. 71 g of a white solid are obtained (i.e. a yield of 80%).

The product has the expected 1H NMR spectrum. 1H NMR (D2O, ppm/TMS): 1.27 (4H, m); 1.48 (4H, m); 1.61 (4H, m); 1.70 (8H, m); 2.85 (6H, 5); 3.16 (12H, m). This 1H NMR spectrum corresponds to that of 1,6-bis(methylpiperidinium)hexane dibromide.

18.9 g of $Ag_2O$ (0.08 mol, 99%, Aldrich) are placed in a 250 ml Teflon beaker containing 30 g of 1,6-bis(methylpiperidinium)hexane dibromide (0.07 mol) and 100 ml of deionized water. The reaction medium is stirred for 12 hours in the absence of light. The mixture is then filtered. The filtrate obtained is composed of an aqueous solution of 1,6-bis(methylpiperidinium)hexane dihydroxide. Assaying of this species is performed by proton NMR using formic acid as standard.

Example 2: Preparation of a Catalyst According to the Invention Containing 2% Cu 0.239 g of an FAU-structure zeolite (CBV712 Zeolyst, $SiO_2/Al_2O_3$=11.42, LOI=12.81) was mixed with 4.952 g of deionized water. 0.573 g of an FAU-structure zeolite (CBV780 Zeolyst, $SiO_2/Al_2O_3$=98.22, LOI=8.52, $P_{ze}$=7170) is added to the previous mixture, and the preparation obtained is kept stirring for 10 minutes. 2.905 g of an aqueous solution of 1,6-bis(methylpiperidinium)hexane dihydroxide (20.91% by weight) prepared according to example 1 are added to the above mixture. The mixture is then kept stirring for 10 minutes. 0.330 g of a 20% by weight aqueous solution of sodium hydroxide (solution prepared from 98% by weight sodium hydroxide, Aldrich) is added to the mixture and kept stirring for 10 minutes. The molar composition of the precursor gel is as follows: 60 $SiO_2$: 1.8 $Al_2O_3$: 10 $R(OH)_2$: 4.3 $Na_2O$: 2204 $H_2O$, i.e. an $SiO_2/Al_2O_3$ ratio of 33.3.

The precursor gel is then transferred, after homogenization, into an autoclave. The autoclave is closed and then heated for 6 days at 180° C. with stirring at 35 rpm with a rotary spit system. The crystalline product obtained is filtered and washed with deionized water.

Heat Treatment Step (Calcination)

The washed solid is dried overnight at 100° C. The loss on ignition (LOI) of the dried solid, evaluated at 1000° C. for 2 hours, is 10.1%.

The dried solid is then introduced into a muffle furnace where a calcination step is performed under a stream of air: the calcination cycle comprises an increase in temperature of 1.5° C./minute up to 200° C., a stationary phase at 200° C. maintained for 2 hours, an increase in temperature of 1° C./minute up to 550° C., followed by a stationary phase at 550° C. maintained for 8 hours, then a return to ambient temperature.

The calcined solid product was analyzed by X-ray diffraction and identified as being constituted of a mixture of approximately 50% by mass of an AFX-structure zeolite and 50% by mass of a BEA-structure zeolite. The AFX-BEA mixture represents approximately 100% by mass of the product obtained.

$NH_4^+$ Ion Exchange on the Calcined AFX Zeolite and Heat Treatment

The calcined AFX-BEA composite material is brought into contact with a 3 molar $NH_4NO_3$ solution for 1 hour with stirring at 80° C. The ratio between the volume of $NH_4NO_3$ solution and the mass of solid is 10. The solid obtained is filtered off and washed and the exchange procedure is repeated twice more under the same conditions. The final solid is separated, washed with deionized water and dried at 100° C. for 4 hours.

The AFX-BEA composite material in ammoniacal form is treated under a stream of air at 550° C. for 8 hours with a temperature increase gradient of 1° C./min. The loss on ignition (LOI) of the solid obtained, evaluated at 1000° C. for 2 hours, is 4% by weight. The product obtained is an AFX-BEA composite material in protonated form.

Cu Ion Exchange and Heat Treatment

The calcined AFX-BEA composite material is brought into contact with a solution of $[Cu(NH_3)_4](NO_3)_2$ for 1 day with stirring at ambient temperature. The final solid is separated, washed with deionized water and dried at 100° C. for 4 hours.

The exchanged and dried solid, obtained after the bringing into contact with the solution of $[Cu(NH_3)_4](NO_3)_2$, is calcined under a stream of air at 550° C. for 8 hours.

Figure 2:
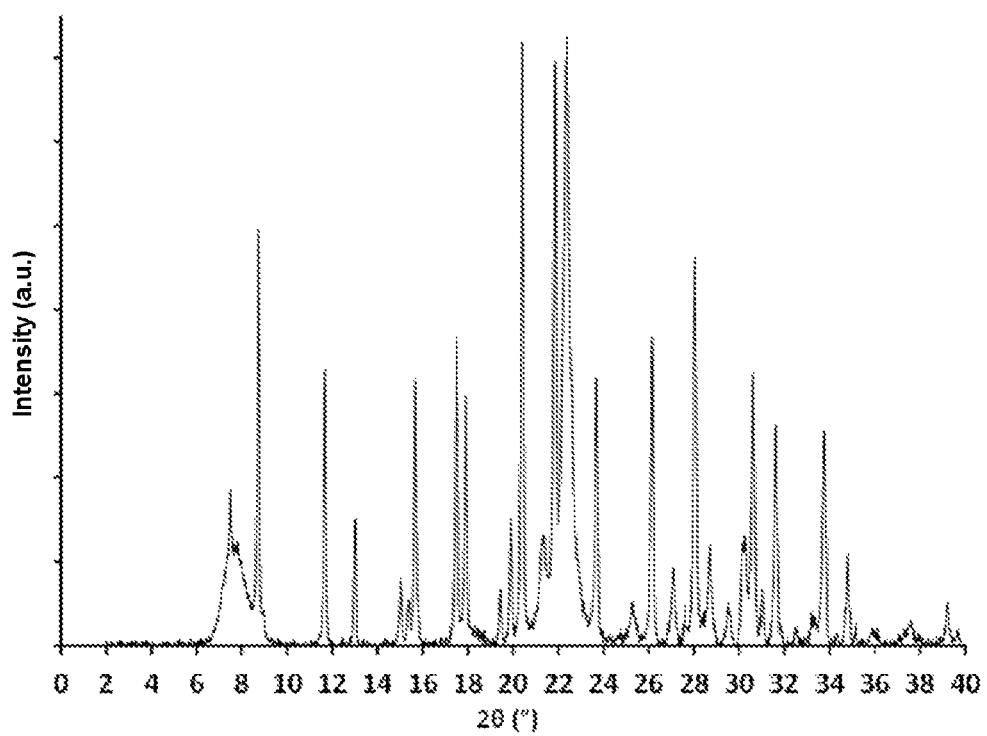
FIG. 2 represents the X-ray diffraction pattern of the Cu-AFX-BEA catalyst obtained according to example 2.

The calcined solid product is analyzed by X-ray diffraction (cf. FIG. 2) and identified as being constituted of a mixture of approximately 50% by mass of an AFX-structure zeolite and 50% by mass of a BEA-structure zeolite. The AFX-BEA mixture represents 98% by mass of the product obtained. The copper content represents a percentage by mass of 2% as determined by X-ray fluorescence.

The catalyst obtained is denoted Cu-AFX-BEA.

Example 3: NOx Conversion Under Standard-SCR Conditions

A catalytic test of nitrogen oxide (NOx) reduction by ammonia ($NH_3$) in the presence of oxygen ($O_2$) under Standard-SCR conditions is carried out at different operating temperatures for the catalyst synthesized according to example 2 (Cu-AFX-BEA).

200 mg of catalyst in powder form are placed in a quartz reactor. 145 l/h of a representative load of a mixture of exhaust gas from a diesel engine are fed into the reactor. This load has the following molar composition: 400 ppm NO, 400 ppm $NH_3$, 8.5% $O_2$, 9% $CO_2$, 10% $H_2O$, remainder $N_2$.

An FTIR analyzer is used to measure the concentration of the species NO, $NO_2$, $NH_3$, $N_2O$, CO, $CO_2$, $H_2O$, $O_2$ at the reactor outlet. The NOx conversions are calculated as follows:

Conversion=(NOx inlet−NOx outlet)/NOx inlet

The results, in particular the catalyst initiation temperatures, are given below for the Standard-SCR conditions:

| | T50 | T80 | T90 | T100 |
|---|---|---|---|---|
| Cu-AFX-BEA | 196° C. | 238° C. | 280° C. | 400° C. |

T50 corresponds to the temperature at which 50% of the NOx in the gas mixture are converted by the catalyst. T80 corresponds to the temperature at which 80% of the NOx in the gas mixture are converted by the catalyst. T90 corresponds to the temperature at which 90% of the NOx in the gas mixture are converted by the catalyst. T100 corresponds to the temperature at which 100% of the NOx in the gas mixture are converted by the catalyst.

It appears that the Cu-AFX-BEA catalyst synthesized according to the invention makes it possible to efficiently convert NOx over the whole of the temperature range tested. A maximum conversion of 100% is reached at 400° C. The initiation temperatures obtained with the Cu-AFX-BEA catalyst according to the invention are satisfactory: they are in fact low, in particular for the degrees of conversion of 50%, 80% and 90%.

The invention claimed is:

1. A process for preparing a catalyst comprising a mixture of AFX-structure and BEA-structure zeolites, and at least one transition metal, comprising at least the following steps:
   i) mixing, in aqueous medium, a first FAU zeolite having an $SiO_2/Al_2O_3$ molar ratio of between 30 and 100 and at least one second FAU-structure zeolite having an $SiO_2/Al_2O_3$ molar ratio of greater than or equal to 2 and less than 30, and wherein the mathematical parameter, $P_{ze}$, corresponding to the mass percentage of the FAU zeolite with an $SiO_2/Al_2O_3$ molar ratio of between 30 and 100, in its anhydrous form (expressed in %) in the mixture of FAU zeolites, multiplied by the $SiO_2/Al_2O_3$ molar ratio of the same FAU zeolite with an $SiO_2/Al_2O_3$ molar ratio of between 30 and 100, is such that: $3250<P_{ze}<7200$, of at least one nitrogenous organic compound R, chosen from 1,5-bis(methylpiperidinium)pentane dihydroxide, 1,6-bis(methylpiperidinium)hexane dihydroxide, 1,7-bis(methylpiperidinium)heptane dihydroxide, and mixtures thereof, and of at least one source of at least one alkali metal and/or alkaline-earth metal M of valence n, n being an integer greater than or equal to 1, the reaction mixture having the following molar composition:

$(SiO_{2(FAU)})/(Al_2O_{3(FAU)})$ of between 30 and 80,
$H_2O/(SiO_{2(FAU)})$ of between 1 and 100,
$R/(SiO_{2(FAU)})$ of between 0.01 and 0.6,
$M_{2/n}O/(SiO_{2(FAU)})$ of between 0.005 and 0.45,
wherein $SiO_{2(FAU)}$ is the molar amount of $SiO_2$ provided by all the FAU-structure zeolites introduced into the mixture, $Al_2O_{3(FAU)}$ is the molar amount of $Al_2O_3$ introduced by all the FAU-structure zeolites introduced into the mixture, $H_2O$ the molar amount of water present in the reaction mixture, R the molar amount of the nitrogenous organic compound, $M_{2/n}O$ being the molar amount of $M_{2/n}O$ provided by all the FAU zeolites and by the source of alkali metal and/or alkaline-earth metal, until a precursor gel is obtained;

ii) hydrothermal treatment of the precursor gel obtained at the end of step i) at a temperature of between 120° C. and 220° C., for a period of between 12 hours and 15 days, to obtain a solid crystalline phase, termed "solid";

iii) at least one ion exchange comprising bringing the solid obtained at the end of the previous step into contact with at least one solution comprising at least one species that is capable of releasing a transition metal, in solution in reactive form, with stirring at ambient temperature for a period of between 1 hour and 2 days;

iv) heat treatment by drying the solid obtained at the end of the previous step at a temperature of between 20 and 150° C. for a period of between 2 and 24 hours, followed by calcination under a stream of air at a temperature of between 450 and 700° C. for a period of between 2 and 20 hours.

2. The process as claimed in claim 1, wherein steps iii) and iv) are reversed, and optionally repeated.

3. The process as claimed in claim 1, wherein step iii) is carried out by bringing the solid into contact with a solution comprising at least one species, preferably a single species, capable of releasing a transition metal or by successively bringing the solid into contact with different solutions each comprising at least one, preferably a single, species capable of releasing a transition metal, the different solutions advantageously comprising different species capable of releasing a transition metal.

4. The process as claimed in claim 1, wherein the transition metal released in the solution of step iii) is selected from the group made up of the following elements: Ti, V, Mn, Mo, Fe, Co, Cu, Cr, Zn, Nb, Ce, Zr, Rh, Pd, Pt, Au, W, Ag.

5. The process as claimed in claim 1, wherein the transition metal content is between 0.5 and 6% by mass relative to the total mass of the final catalyst, in its anhydrous form, the amount of copper in the composite material of the catalyst being taken into account.

6. The process as claimed in claim 1, wherein the catalyst contains only copper as transition metal, in a mass content of between 0.5 and 6%, preferably between 0.5 and 5% relative to the total mass of the final catalyst in its anhydrous form.

7. The process as claimed in claim 1, wherein the catalyst comprises copper and another transition metal, the copper content of the catalyst obtained is between 0.05 and 2% by mass, and that of the other transition metal between 1 and 4% by mass, the transition metal contents being given as percentages by mass relative to the total mass of the final catalyst in its anhydrous form.

8. The process as claimed in claim 1, wherein the catalyst contains only iron as transition metal, in a mass content of between 0.5 and 5 relative to the total mass of the final catalyst in its anhydrous form.

9. The process as claimed in claim 1, wherein the catalyst comprises iron and another transition metal, the iron content of the catalyst obtained is between 0.05 and 2% by mass, and that of the other transition metal is between 1 and 4% by mass, the transition metal contents being given as percentages by mass relative to the total mass of the final catalyst in its anhydrous form.

10. The process as claimed in claim 1, for which the nitrogenous organic compound R is 1,6-bis(methylpiperidinium)hexane dihydroxide.

11. The process as claimed in claim 1, wherein the hydrothermal treatment of step ii) is carried out at a temperature of between 150° C. and 195° C. for a period of between 12 hours and 8 days.

12. The process as claimed in claim 1, for which the heat treatment step iv) comprises drying the solid at a temperature of between 60 and 100° C. for a period of between 2 and 24 hours, followed by calcining, corresponding to a treatment by combustion in air, which is optionally dry, at a temperature of between 500 and 600° C. for a period of between 6 and 9 hours, the flow rate of optionally dry air being between 0.5 and 1.5 l/h/g of solid to be treated.

13. A catalyst comprising a composite material comprising an intimate mixture of a zeolite of AFX type and a zeolite of BEA type, and at least one transition metal, having a zeolite structure comprising:

between 30 and 90% by mass by mass of AFX-structure zeolite, relative to the total mass of the catalyst in its anhydrous form;

between 10 and 70% by mass by mass of BEA-structure zeolite, relative to the total mass of the catalyst in its anhydrous form;

wherein the transition metal is selected from the group made up of the following elements: Ti, V, Mn, Mo, Fe, Co, Cu, Cr, Zn, Nb, Ce, Zr, Rh, Pd, Pt, Au, W, Ag or a mixture thereof, wherein the total content of transition metals is between 0.5 and 6% by mass relative to the total mass of the final catalyst, in its anhydrous form, and wherein the catalyst comprises less than 10% by mass of impurities and/or of crystalline or amorphous phase other than AFX and BEA.

14. The catalyst as claimed in claim 13, containing only copper as transition metal and wherein the total copper content by mass is between 0.5 and 6 relative to the total mass of the final catalyst in its anhydrous form.

15. The catalyst as claimed in claim 13, comprises copper and another transition metal, and wherein the copper content is between 0.05 and 2% by mass, while the content of the other transition metal is between 1 and 4% by mass, the transition metal contents being given as percentages by mass relative to the total mass of the final catalyst in its anhydrous form.

16. The catalyst as claimed in claim 13, containing only iron as transition metal and wherein the total iron content by mass is between 0.5 and 5% relative to the total mass of the final catalyst in its anhydrous form.

17. The catalyst as claimed in claim 13, comprises iron and another transition metal, and wherein the iron content is between 0.05 and 2% by mass, while the content of the other transition metal is between 1 and 4% by mass, the transition metal contents being given as percentages by mass relative to the total mass of the final catalyst in its anhydrous form.

18. The use of the catalyst as claimed in claim 13 for the selective reduction of $NO_x$ by a reducing agent such as $NH_3$ or $H_2$.

19. The use as claimed in claim 18, for which the catalyst is formed by deposition in the form of a coating on a monolith.

20. The use as claimed in claim 19, for which the honeycomb structure is formed by parallel channels open at both ends or comprises porous filtering walls for which the adjacent parallel channels are alternately blocked at both ends of the channels.

21. The use as claimed in claim 20, for which the amount of catalyst that is deposited on the structure is between 50 and 180 g/l for the filtering structures and between 80 and 200 g/l for the structures with open channels.

22. The use as claimed in claim 18, for which the catalyst is combined with a binder such as ceria, zirconium oxide, alumina, non-zeolitic silica-alumina, titanium oxide, a ceria-zirconia mixed oxide, a tungsten oxide and/or a spinel in order to be formed by deposition in the form of a coating.

23. The use as claimed in claim 18, for which the coating is combined with another coating having the capacity to adsorb pollutants, in particular NOx, to reduce pollutants, in particular NOx, or to promote the oxidation of pollutants.

24. The use as claimed in claim 18, for which the catalyst is in the form of an extrudate containing up to 100% of the catalyst.

25. The use as claimed in claim 18, for which the structure coated with the catalyst or obtained by extrusion of the catalyst is integrated into an exhaust line of an internal combustion engine.

26. A catalyst comprising a composite material comprising an intimate mixture of a zeolite of AFX type and a zeolite of BEA type, and at least one transition metal, having a zeolite structure comprising:
   between 30 and 90% by mass by mass of AFX-structure zeolite, relative to the total mass of the catalyst in its anhydrous form;
   between 10 and 70% by mass of BEA-structure zeolite, relative to the total mass of the catalyst in its anhydrous form;
   wherein the transition metal is selected from the group made up of the following elements: Ti, V, Mn, Mo, Fe, Co, Cu, Cr, Zn, Nb, Ce, Zr, Rh, Pd, Pt, Au, W, Ag or a mixture thereof,
   wherein the total content of transition metals is between 0.5 and 6% by mass relative to the total mass of the final catalyst, in its anhydrous form,
   wherein the catalyst comprises less than 10% by mass of impurities and/or of crystalline or amorphous phase other than AFX and BEA, and
   wherein the catalyst is obtained by the process as claimed in claim 1.

27. The use of the catalyst as claimed in claim 26 for the selective reduction of $NO_x$ by a reducing agent such as $NH_3$ or $H_2$.

* * * * *